US010034647B2

(12) United States Patent
Liang et al.

(10) Patent No.: US 10,034,647 B2
(45) Date of Patent: Jul. 31, 2018

(54) SYSTEM AND METHOD FOR ENDOSCOPIC X-RAY LUMINESCENCE COMPUTED TOMOGRAPHIC IMAGING

(75) Inventors: Jimin Liang, Xi'an (CN); Xueli Chen, Xi'an (CN); Xiaochao Qu, Xi'an (CN); Shouping Zhu, Xi'an (CN); Duofang Chen, Xi'an (CN); Heng Zhao, Xi'an (CN); Jie Tian, Xi'an (CN)

(73) Assignee: XIDIAN UNIVERSITY, Xi'an (CN)

( * ) Notice: Subject to any disclaimer, the term of this patent is extended or adjusted under 35 U.S.C. 154(b) by 978 days.

(21) Appl. No.: 14/379,732

(22) PCT Filed: Mar. 16, 2012

(86) PCT No.: PCT/CN2012/072434
§ 371 (c)(1),
(2), (4) Date: Nov. 14, 2014

(87) PCT Pub. No.: WO2013/134949
PCT Pub. Date: Sep. 19, 2013

(65) Prior Publication Data
US 2015/0119700 A1    Apr. 30, 2015

(51) Int. Cl.
*A61B 6/00* (2006.01)
*A61B 6/12* (2006.01)
(Continued)

(52) U.S. Cl.
CPC .......... *A61B 6/5247* (2013.01); *A61B 5/0086* (2013.01); *A61B 6/032* (2013.01); *A61B 6/12* (2013.01); *A61B 6/485* (2013.01)

(58) Field of Classification Search
CPC ....... A61B 6/5247; A61B 6/032; A61B 6/485; A61B 6/12; A61B 5/0086
See application file for complete search history.

(56) References Cited

U.S. PATENT DOCUMENTS

| 5,987,351 | A  | * | 11/1999 | Chance ............... | A61B 5/0077 600/473 |
| 7,236,558 | B2 |   | 6/2007  | Saito et al.         |                     |
| 2007/0238957 | A1 | * | 10/2007 | Yared ................ | A61B 5/0059 600/407 |

FOREIGN PATENT DOCUMENTS

| CN | 101467887 A | 7/2009 |
| CN | 101594825 A | 12/2009 |

(Continued)

OTHER PUBLICATIONS

International Search Report, dated Dec. 27, 2012, for PCT/CN2012/072434, 4 pages.

(Continued)

*Primary Examiner* — Peter Luong
(74) *Attorney, Agent, or Firm* — Seed IP Law Group LLP (57) ABSTRACT

A system for the endoscopic X-ray luminescence computed tomographic imaging is provided. The system comprises an excitation source unit (1) configured to excite a probe inside a detecting object from an external excitation source; a signal collecting unit (2) configured to collect X-ray images of the detecting object and near-infrared light signal images emitting from the probe being excited; a computing unit (4) configured to preprocess the collected X-ray images and the near-infrared light signal images, execute sparse reconstruction on the preprocessed X-ray images so as to obtain anatomical structure information of the detecting object and location information of an endoscopic detector in the signal collecting unit (2) inside the detecting object, and use the obtained anatomical structure information and the location information to execute three-dimensional optical reconstruction based on the preprocessed near-infrared light signal images so as to obtain localization and distribution of an imaging target inside the detecting object.

19 Claims, 6 Drawing Sheets

(51) Int. Cl.
    *A61B 5/00*         (2006.01)
    *A61B 6/03*         (2006.01)

(56) References Cited

FOREIGN PATENT DOCUMENTS

| | | |
|---|---|---|
| CN | 201879710 U | 6/2011 |
| WO | 2011137538 A1 | 11/2011 |

OTHER PUBLICATIONS

Piao et al., "Endoscopic, rapid near-infrared optical tomography," Optics Letters 31(19):2876-2878, Oct. 1, 2006.

Carpenter et al., "Hybrid x-ray/optical luminescence imaging: Characterization of experimental conditions," Medical Physics, 37(8):4011-4018, Aug. 2010.

Carpenter et al., "Limited angle x-ray luminescence tomography: methodology and feasibility study," Physics in Medicine and Biology 56:3487-3502, May 23, 2011.

Chen et al., "Feasibility study of endoscopic x-ray luminescence computed tomography: Simulation demonstration and phantom application," J. Appl. Phys. 114:084701 (2013), 6 pages.

Cong et al., "X-ray micro-modulated luminescence tomography (XMLT)," Optics Express 22(5):5572-5580, Mar. 10, 2014.

Cong et al., "X-ray micromodulated luminescence tomography in dual-cone geometry," Journal of Biomedical Optics 19(7):076002-1 to 076002-5, Jul. 2014.

Pratx et al., "Tomographic molecular imaging of x-ray-excitable nanoparticles," Optics Letters 35(20):3345-3347, Oct. 15, 2010.

Pratx et al., "X-Ray Luminescence Computed Tomography via Selective Excitation: A Feasibility Study," IEEE Transactions on Medical Imaging 29(12):1992-1999, Dec. 2010.

\* cited by examiner

SYSTEM AND METHOD FOR ENDOSCOPIC X-RAY LUMINESCENCE COMPUTED TOMOGRAPHIC IMAGING

TECHNICAL FIELD

This invention relates generally to a field of medical imaging technology, and more particular, to a system and a method for endoscopic X-ray luminescence computed tomographic imaging.

BACKGROUND

Fluorescence diffuse optical tomography (FDOT) has become a potential molecular imaging technology due to an ability of three-dimensional (3D) reconstructing localization and distribution of fluorescent probes in biological tissues. For its potential applications, FDOT has been widely applied to small animals or superficial organ imaging, such as brain and breast. In this case, fluorescent signals can penetrate the imaging object and be acquired by an external detection device. However, due to high attenuation of the fluorescent signals, FDOT cannot provide accurate images, and the signals cannot penetrate the imaging object so that nothing can be measured on the object surface, when a region of interest is buried in deep tissue for big animals or humans.

Endoscopic imaging technique may overcome this limitation and obtain accurate images of the internal organs by providing a detector closer to the region of interest through an organ cavity with a minimally invasive manner, such as intestines, esophagus, gastropore, bladders, and the like. Considering the advantage of endoscopic imaging technique, a system and a method for endoscopic fluorescence diffuse optical tomography (eFDOT) was disclosed by Dr. Daqing Piao, for imaging internal organs of living body (Daqing Piao, Hao Xie, Weili Zhang, and Jerzy S. Kfasinski, "Endoscopic rapid near-infrared optical tomography," Optics Letters, 2006, 31(19), 2876-2878).

However, there are several problems in the conventional eFDOT system for its actual applications, which limits its further clinical applications.

Firstly, existence of autofluorescence induced by external near-infrared light excitation degrades the quality of reconstructed images, and a thorny problem also inherent in FDOT. The autofluorescence is usually be removed by using the image post-processing algorithms. However, it cannot be eliminated essentially and the effect much depends on performance of the algorithm.

Next, a miniaturized endoscopic detector with a diameter of several centimeters may be adopted in the conventional eFDOT apparatus, in which excitation source fibers and detector fibers are distributed evenly and across from each other on sides of a head of the endoscopic detector. Due to a small distance between the excitation source fibers and the detector fibers, strong inference occurs between the signals so as to generate an inaccurate image.

Lastly, diffusion equation (DE) is used as a forward light transport model in the conventional eFDOT method. Because of its inherent limitation, DE cannot accurately describe light propagation in a living body, especially for regions of low scattering, boundaries of light source, and tissues with mismatched refractive index. Therefore, DE cannot be applied in the eFDOT method.

Recently, an emerging molecular imaging modality termed X-ray luminescence computed tomography (XLCT) has been used as a means of imaging small-animal-sized objects. With characteristics of phosphor nanoparticles (PNP) being stimulated by X-rays to emit near-infrared light, XLCT employs an X-ray beam as an excitation light and uses a charge coupled device (CCD) to measure the emitted near-infrared light and further reconstruct the distribution of PNP in a small-animal-sized object using near-infrared 3D optical tomographic imaging technology. Using the X-ray as the excitation source to excitating the PNP probes positioned in a deep organ, XLCT does not suffer from the autofluorescence contribution. However, XLCT is still only used for small animal and superficial organ imaging due to a penetration depth of near-infrared light.

SUMMARY

The presented embodiment of this invention provides both a system and a method for endoscopic X-ray luminescence computed tomographic imaging (eXLCT), to accurately image internal targets inside a detecting object.

According to one aspect of the presented embodiment, an eXLCT imaging system is provided. The system comprises an excitation source unit configured to excite a probe inside a detecting object from an external excitation source; a signal collecting unit configured to collect X-ray images of the detecting object and near-infrared light signal images emitting from the probe being excitated; a computing unit configured to preprocess the collected X-ray images and near-infrared light signal images, and execute sparse reconstruction on the preprocessed X-ray images so as to obtain anatomical structure information of the detecting object and location information of an endoscopic detector in the signal collecting unit inside the detecting object. The obtained anatomical structure information and the location information may be used to execute three-dimensional (3D) optical reconstruction on the preprocessed near-infrared light signal images so as to obtain localization and distribution of an imaging target inside the detecting object.

According to a preferred embodiment, the signal collecting unit may comprise a near-infrared signal collection module, comprising a balloon imaging catheter, an endoscopic detector, a signal transmission fiber bundle and a photomultiplier tube array detector.

According to a preferred embodiment, the balloon imaging catheter may comprise a medical catheter; connected to an air delivery pipe in the signal transmission fiber bundle at one end, and fastened to an outer surface of the signal transmission fiber bundle at other end. The endoscopic detector is wrapped by the medical catheter, wherein the medical catheter is configured to be filled with air to hold up a cavity organ when collecting the near-infrared light signal images.

According to a preferred embodiment, the imaging system further comprises a control unit, comprising a C-shaped rotating arm configured to collect the X-ray images of the object from different angles and an object fixed bed configured to fix the detecting object and be adjusted to fit a field of X-ray imaging.

According to a preferred embodiment, the endoscopic detector may comprise N pairs of drum lens and rod lens. Each pair of drum lens and rod lens is connected to a signal transmission fiber in the signal transmission fiber bundle, and configured to collect the emitted near-infrared light signal images from the probe.

According to a preferred embodiment, the signal transmission fiber bundle may comprise N number of signal transmission fibers configured to transmit the collected near-infrared light signal images to the photomultiplier tube array detector and an air delivery pipe configured to fill the balloon imaging catheter with air.

According to a preferred embodiment, the probe may be a phosphor nanoparticles (PNP) probe.

According to a preferred embodiment, the computing unit is configured to display results of 3D optical reconstruction obtained by fusing the reconstructed images inside the detecting object and the corresponding structural information, so as to three-dimensionally display a fused image.

According to a preferred embodiment, the computing unit may comprise an image preprocessing module configured to preprocess the X-ray images by at least one of noise elimination, dead pixel compensation, and image correction.

According to a preferred embodiment, the computing unit may comprise an image preprocessing module configured to preprocess the near-infrared light signal images by at least one of noise elimination, dead pixel compensation, and extraction of a region of interest.

According to a preferred embodiment, the computing unit may comprise an image reconstruction module configured to: construct a forward hybrid light transport model; establish a total system equation for the eXLCT based on the forward hybrid light transport model, to obtain calculation vectors of the near-infrared light signal images; formulate a sparse regularization objective function based on a difference between the calculation vectors of the NIR light signal images and related measurement vectors, and a combination of the sparse distribution and nonnegative constrains of the probe; optimize the objective function to obtain a spatial location and distribution of the probe inside the detecting object, indicating the location and distribution information of imaging target.

According to a preferred embodiment, the image reconstruction module is configured to construct the forward hybrid light transport model by classifying biological tissues into low scattering, high scattering, and cavity tissues according to location information of the endoscopic detector inside the detecting object and optical properties of tissues; modeling the near-infrared light propagation in the tissues with following three propagation equations: a third-order simplified spherical harmonics equation ($SP_3$), a diffusion equation (DE) and a free space light transport equation (FSE) respectively; and constructing a boundary coupling condition to couple the propagation equations and constructing the forward hybrid light transport model for eXLCT along with the excitation of the probe by the X-ray beam.

According to a preferred embodiment, the image reconstruction module is configured to establish the total system equation by:

executing discretization on the constructed forward hybrid light transport model based on a finite element method, to obtain sub system equations on each discretized element:

assembling the sub system equations as follows:

$$A_k \rho = P_k$$

where $A_k$ is a system matrix corresponding to the kth X-ray illuminating angle, depending on the distribution of the tissues in a living body, optical properties, and location of the X-ray illuminating at a body surface; $\rho$ is a concentration of the probe; $P_k$ is a calculated intensity of the NIR light at the endoscopic detector corresponding to the kth X-ray illuminating angle;

establishing the total system equation for eXLCT by combining M sub system equations corresponding to M X-ray illuminating angles, respectively:

$$A\rho = P$$

where A is the total system matrix and defined as $A=[A_1, A_2, \ldots, A_M]^T$, T is a matrix transposition operator; P is a matrix of calculated intensity of the NIR light at endoscopic detector corresponding to M X-ray illuminating angles, defined as $P=[P_1, P_2, \ldots, P_M]^T$; M is the number of X-ray illuminating angles.

According to a preferred embodiment, the image reconstruction module is configured to calculate $\rho$ as a sparse regularization objective function established by using a following equation:

$$\rho = \arg \min_{\rho \geq 0} \ \|A\rho - P^m\|_1 + \lambda \|\rho\|_1$$

where $P^m$ is a measurement vector of NIR light signals detected by the endoscopic detector corresponding to M X-ray illuminating angles; $\lambda$ is a sparse regularization parameter; $\|F\|_1$ is $l_1$ norm of the matrix F;

solve the sparse regularization objective function, to obtain a spatial location and a concentration distribution of the probe, indicating the location and distribution information of the target inside the detecting object.

According to a preferred embodiment, the biological tissues may be classified according to rules of defining the low scattering tissues as regions where the probe locates, the body surface belongs, and a ratio of the reduced scattering coefficient to absorbing coefficient is less than 10; defining the high scattering tissues as regions where the ratio of the reduced scattering coefficient to absorbing coefficient is larger than 10, and defining the cavity as the tissue where the endoscopic detector locates when collecting the near-infrared light signal images.

According to a preferred embodiment, the image reconstruction module is further configured to model the near-infrared light propagation in the tissues comprises: using $SP_3$ to characterize the near-infrared light propagation in the low scattering tissues; using DE to characterize the high scattering tissues; and using FSE to characterize a near-infrared light transport from the boundary between the scattering tissues and cavity to the endoscopic detector.

According to a preferred embodiment, modeling the near-infrared light propagation in the tissues comprises: using a formula as follows to couple equations of $SP_3$ and DE, which characterize the near-infrared light propagation in the low and high scattering tissues respectively:

$$\Phi(r) = \alpha(r)(\beta_1(r)\phi_1(r) + \beta_2(r)\phi_2(r))$$

where r is an arbitrary point on the boundary of low and high scattering tissues; $\Phi(r)$ is a light flux at r calculated by the DE; $\phi_1(r)$ and $\phi_2(r)$ are light flux components at r calculated by the $SP_3$; $\alpha(r)$ is a mismatched refractive index of the DE; $\beta_1(r)$ and $\beta_2(r)$ are mismatched refractive indexes of the $SP_3$.

According to a preferred embodiment, modeling the near-infrared light propagation in the tissues comprises using a formula as follows to couple the light transport equations of scattering tissues and cavity:

$$J(r) = \sigma\left(\frac{1}{\alpha(r)}\Phi(r)\right) + (1-\sigma)(\beta_1(r)\phi_1(r) + \beta_2(r)\phi_2(r))$$

where r is an arbitrary point at the boundary of the scattering and cavity tissues; J(r) is a light flux rate at r and points inward of cavity; $\sigma$ is an identify factor of scattering tissues, which is 0 if the low scattering tissue intersects with the cavity, and is 1 if the high scattering tissue intersects with the cavity.

According to another aspect of the presented invention, an eXLCT imaging method is provided, comprising steps of: (a) collecting near-infrared light signal images emitted from a probe and X-ray images of a detecting object (b) preprocessing the collected near-infrared light signal images and the X-ray images; (c) executing sparse reconstruction on the preprocessed X-ray images to obtain structural information of a detecting object and localization information of an endoscopic detector; (d) executing 3D optical reconstruction on the preprocessed near-infrared light signal images by using the obtained structure information of the detecting object and the localization information of the endoscopic detector, so as to obtain location and distribution information of the target inside the detecting object.

The present invention may take advantages as follows.

Firstly, the interference problem of strong autofluorescence induced by the external near-infrared light excitation source in the conventional technology is addressed by utilizing the X-ray beam as an external excitation to excite the PNP probe inside the detecting object. Therefore, high quality near-infrared light images can be acquired, which would improve the quality of reconstructed image effectively.

Secondly, signal interference and imaging inaccuracy caused by the fact that the exciting sources and detectors are circularly distributed at the head of miniaturized endoscopic detector can be overcome by utilizing X-ray beam as the external excitation to excite the PNP probe inside the detecting object and using the endoscopic detector as the internal detector to collect the emitted near-infrared light signal emitted from the PNP probe. This can improve signal interference and imaging accuracy of an endoscopic optical tomography in an excitation mode.

Thirdly, in the case of using a hybrid light transport model as the forward model of eXLCT imaging method and meanwhile, establishing a sparse regularization objective function in consideration of sparse distribution of the PNP probe and sparse property of the endoscopic measurements with respect to solving domain of living body, the problems of the in inaccuracy and resolution insufficiency induced by using the DE as the forward model and $l_2$ regularization method may be addressed, which effectively improve the accuracy and resolution of eXLCT imaging method.

Furthermore, because the endoscopic detector is used as the internal detector to collect the emitted near-infrared light signal emitted from the PNP probe, the limitation of XLCT in the small animals or superficial organs may be alleviated, so that an accurate image of the deep target inside a large animal or human may be achieved.

BRIEF DESCRIPTION OF THE DRAWINGS

A more particular description of the invention will be rendered with reference to the accompanying drawings. The invention will be described and explained in detail through the use of the accompanying drawings, in which.

DETAILED DESCRIPTION

The preferred embodiments of this invention are described in detail with reference to the accompanying drawings. This illustration of the embodiment depicts only typical embodiments of the invention and is not therefore to be considered to be limiting of its scope.

According to an embodiment of the invention, an X-ray tube is selected as an excitation source to excite the PNP probe inside the detecting object, and a miniature endoscopic detector is used as a detector to collect near-infrared light signal emitted from the PNP probe. A flat panel detector that is colinear with the X-ray tube and fixed bed of detecting object, is used to obtain 3D structural information of the detecting object. A physical model and a forward light transport model for endoscopic X-ray luminescence computed tomographic (eXLCT) imaging are established sequentially based on the imaging system and related imaging process. Based on the forward light transport model, a sparse regularization objective function is established by using a finite element method based on the sparse distribution of the PNP probe and significant insufficiency of the endoscopic measurements. Finally, the objective function is solved by using an appropriate optimization algorithm to obtain accurate images of the internal organs or deep targets in the detecting object.

The eXLCT imaging system according to the presented embodiment is described in detail with reference to FIG. 1, FIG. 2, FIG. 3 and FIG. 4. According to the presented embodiment, the eXLCT imaging system comprises an excitation source unit 1, a sign collecting unit 2, a contra unit 3, and a computing unit 4.

Figure 1:
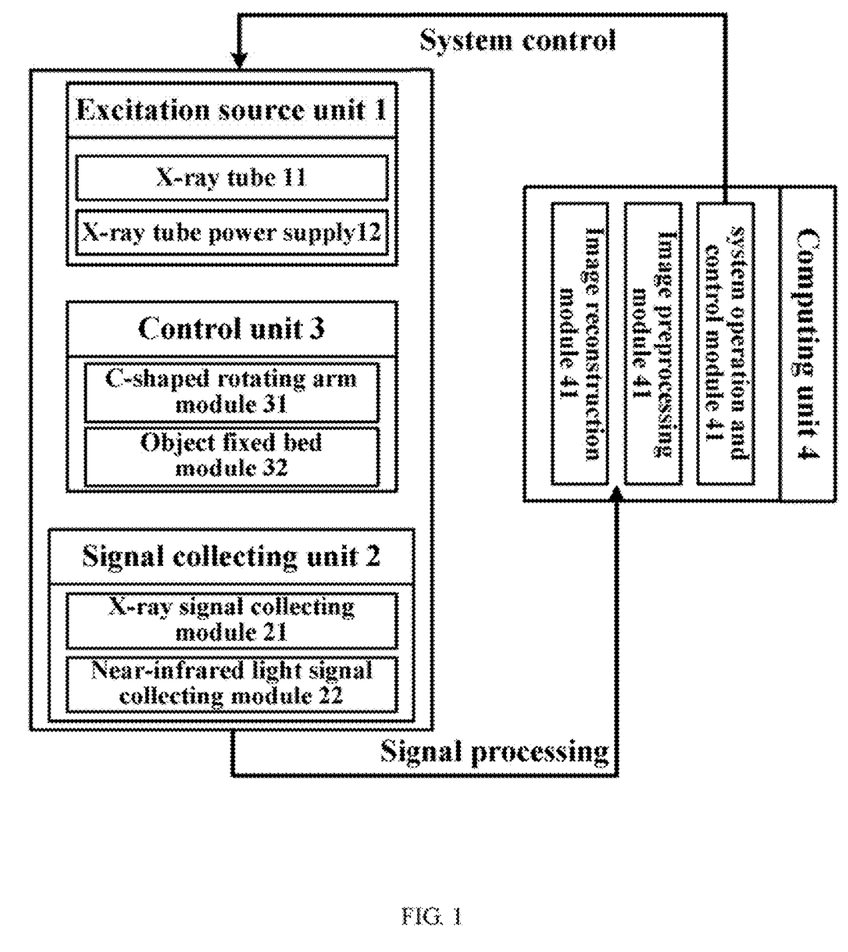
FIG. 1 is a block diagram for the endoscopic X-ray luminescence computed tomographic imaging system according to an embodiment of this invention.
Figure 2:
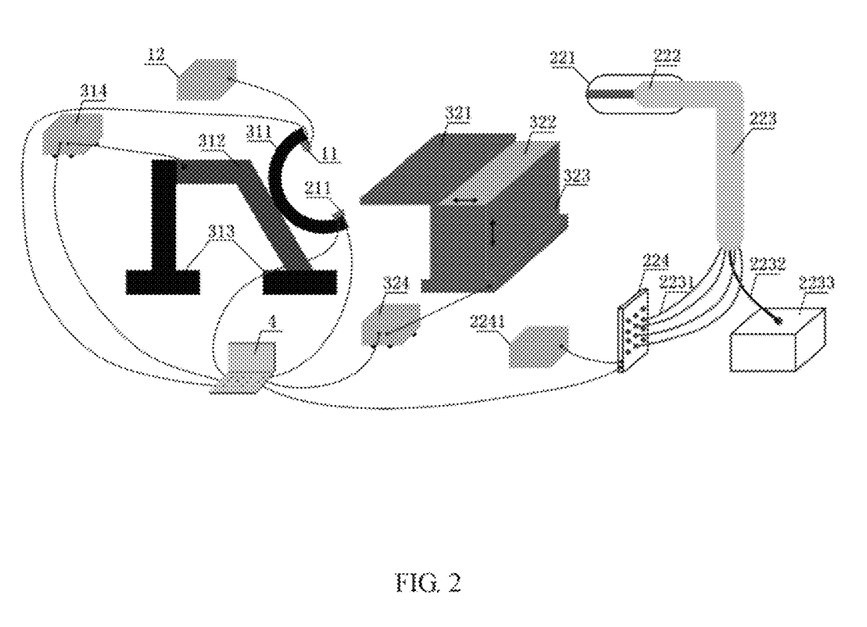
FIG. 2 presents a schematic diagram for the endoscopic X-ray luminescence computed tomographic imaging system according to an embodiment of this invention.

The excitation source unit 1 comprises an X-ray tube 11 and an X-ray tube power supply 12, and is used as an external excitation source to excite the internal PNP probe inside a detecting object and used as a scanning tool to acquire the anatomical information of detecting object as well as the location of the endoscopic detector, in the presented embodiment, the PNP probe is selected as an example. R is obvious for those skilled persons in the art that the probes can also be the other probes, such as a rare earth probe.

Figure 3:
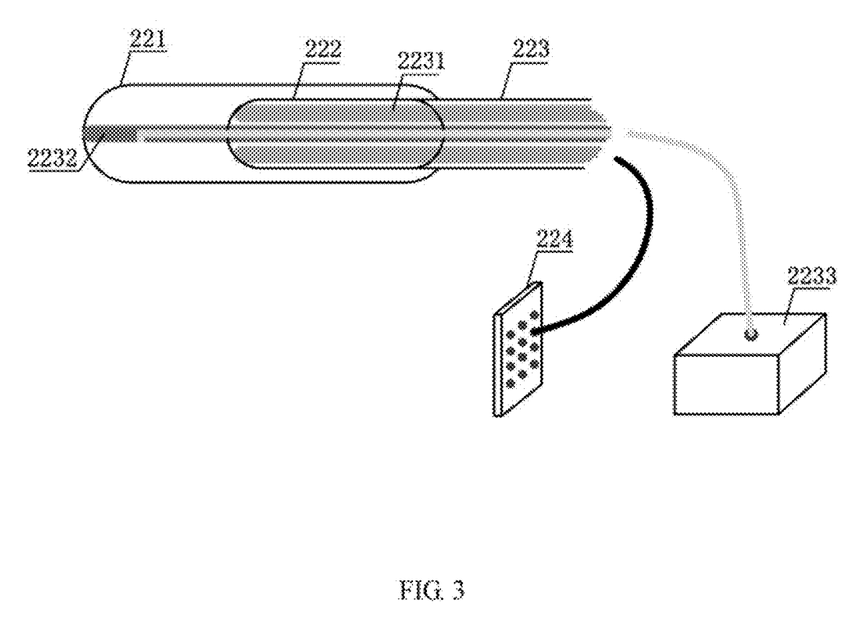
FIG. 3 is a cross-section diagram of near-infrared light signal collection module in the endoscopic X-ray luminescence computed tomographic imaging system according to an embodiment of this invention.

The signal collecting unit 2 comprises an X-ray signal collecting module 21 and a near-infrared (NIR) light signal collecting module 22. The X-ray signal collecting module 21 may comprise an X-ray CMOS flat detector 211 configured to acquire the X-ray images of the detecting object. The NIR light signal collecting module 22 may include a balloon imaging catheter 221, an endoscopic detector 222, a signal transmission fiber bundle 223, and a photomultiplier tubes (PMT) array detector 224, and is configured to endoscopically acquire the NIR light signal from the excited PNP probe.

The control unit 3 comprises a C-shaped rotating arm module 31 and an object fixed bed module 32. The C-shaped rotating arm module 31 may comprise a C-shaped arm 311, a rotating control device 312, a C-shaped arm support pillar 313, and a stepping motor 314, and is configured to acquire the X-ray images of the detecting object from a multitude of angles. The object fixed bed module 32 may comprise an object fixing stage 321, a translational slide rail 322, a lifting platform 323, and a stepping motor 324, and configured to fix the detecting object on the object fixing stage and adjust the position of detecting object in the field of X-ray imaging.

The computing unit 4 may comprise a system operation and control module 41, an image preprocessing module 42, and an image reconstruction module 43.

For example, the structural relations of the aforementioned components may be described as follows.

The X-ray tube 11 and X-ray CMOS flat detector 211 are fixed at each end of the C-shaped arm 311 separately and oppositely. The X-ray tube 11 is connected to the X-ray tube power supply 12 with a power line. At the same time, the X-ray tube 11 is also connected to the computing unit 4 via control lines, to control a switch and an intensity of X-ray signal emitted from the X-ray tube 11. The X-ray CMOS flat detector 211 is connected to the computing unit 4 via the control lines and data cables, to control the acquisition of X-ray signal with the X-ray CMOS flat detector 211 and the signal transmission to the computing unit 4. The C-shaped arm 311 is connected to the rotating control device 312 fixed onto the C-shaped arm support pillar 313. The stepping motor 314 is connected to the rotating control device 312 and the computing unit 4 through the control lines. The C-shaped arm 311 can slide evenly distributed in radian for example, on the rotating control device 312, through controlling the stepping motor 314 with the system operation and control module 41 of computing unit 4.

The object fixing stage 321 is fixed on the translational slide rail 322, while the translational slide rail 322 is coupled to the stepping motor 324 via control lines. In addition, the translational slide rail 322 is fixed on the lifting platform 323, and the lifting platform 323 is coupled to the stepping motor 324 via the control lines as well and the stepping motor 324 is further connected to the computing unit 4 via the control lines.

In operation, the detecting object is first fastened on the object fixing stage 321. The object fixing stage 321 is then moved in a vertical direction by adjusting the lifting platform 323 by controlling the stepping motor 324 with the system operation and control module 41 of computing unit 4. At the same time, the object fixing stage 321 slides in a horizontal direction by adjusting the translational slide rail 322. This guarantees that the object fixing stage 321, the X-ray tube 11, and the X-ray CMOS flat detector 211 are collinear, and that the object fixing stage 321 is always in the radiation field of the X-ray tube 11 and the imaging range of X-ray CMOS flat detector 211 when the C-shaped arm 311 is sliding evenly distributed in radian.

Figure 4:
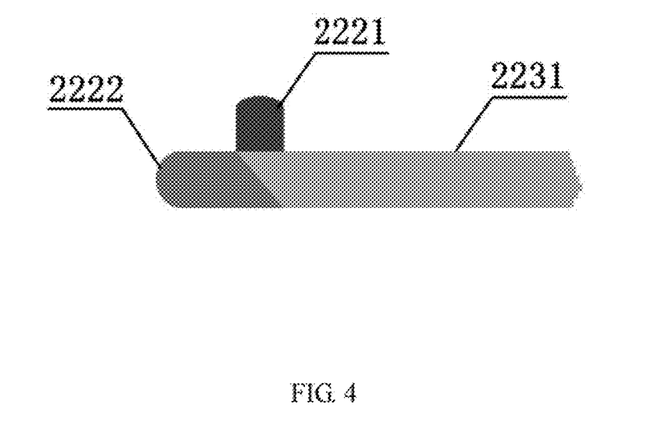
FIG. 4 is a cross-section diagram of endoscopic detector in the endoscopic X-ray luminescence computed tomographic imaging system according to an embodiment of this invention.

In the NIR light signal collecting module 22, the balloon imaging catheter 221 comprises a medical catheter. The medical catheter is connected to an air delivery pipe 2232 in the signal transmission fiber bundle 223 at one end and fastened to outer surface of the signal transmission fiber bundle 223 at the other end. Furthermore, the endoscopic detector 222 is wrapped by the medical catheter which is used to hold up the wall of cavity organs by filling the air when acquiring the NIR light signal images. The endoscopic detector 222 comprises N pairs of drum lens 2221 and rod lens 2222 (for example, N is no less than 60, and N is set to be 60 in this embodiment). Each pair of drum lens 2221 and rod lens 2222 is connected to the signal transmission fibers 2231 in the signal transmission fiber bundle 223, to acquire the NIR light signal emitted from the PNP probe.

The NIR light signal first arrives at the drum lens 2221 and then passes to the rod lens 2222. After interacting with the rod lens 2222, the signal is finally coupled to the signal transmission fibers 2231. A double ring ladder mode is used in the signal transmission fiber bundle 223, where an outer layer is formed with N evenly spaced signal transmission fibers 2231 (for example, N is no less than 60, and N is set to be 60 in this embodiment), while an inner layer is formed with the air delivery pipe 2232. The inner layer is 2 cm longer than the outer layer approximately. The space between the two layers and the outermost shell is parceled with anti-interference materials. One end of the signal transmission fibers 2231 is connected to the drum lens 2221 and rod lens 2222 in the endoscopic detector 222; while the other end is connected to the PMT array detector 224, to transmit the NIR light signal acquired by the endoscopic detector 222 to the PMT array detector 224. Similarly, one end of the air delivery pipe 2232 is connected to the balloon imaging catheter 221, while the other end is connected to the air aerator 2233. A small hole is provided on the air delivery pipe 2232 at position of longer than the signal transmission fibers 2231, to fill air into the balloon imaging catheter 221. The PMT array detector 224 may comprise a group of PMTs arranged square array (for example, the number is no less than 60, and 60 in this embodiment). The PMT array detector 224 is connected to the PMT array detector power supply 2241 via the control lines and to the computing unit 4 via control lines and the data cables.

The system operation and control module 41 of computing unit 4 is configured to control the overall operation of the control unit 3, the excitation source unit 1, and the signal collecting unit 2, to accomplish the control of the rotating control device 312 of C-shaped arm 311, the object fixing stage 321, the X-ray tube 11, the X-ray CMOS flat detector 211 and the NIR light signal collecting module 22, and realize the acquisition of the X-ray images and the NIR light signal images.

The image preprocessing module 42 is configured to preprocess the acquired X-ray images and NIR light signal images, by executing the dead pixel compensation, noise elimination, and image correction for the X-ray images, as well as the dead pixel compensation, noise elimination, and extraction of the region of interest for the NIR light signal images.

The image reconstruction module 43 is configured to carry out the sparse reconstruction of the preprocessed X-ray images, to obtain the anatomical information of detecting object and the location of the endoscopic detector 222; and to conduct 3D optical reconstruction of the preprocessed NIR light signal images, to obtain location and distribution information of the target deep inside the detecting object.

Figure 5:
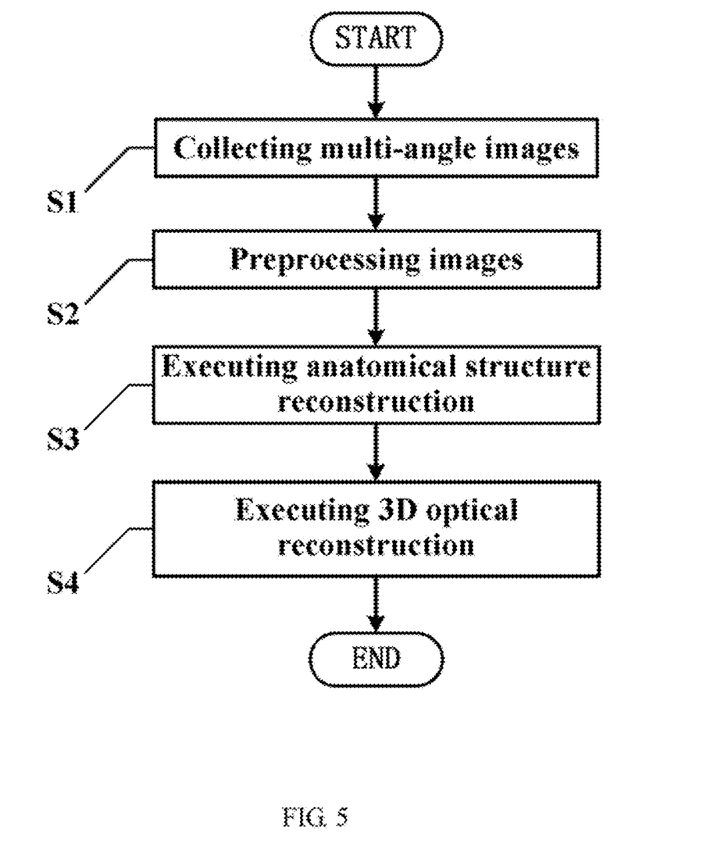
FIG. 5 shows a flow chart for the endoscopic X-ray luminescence computed tomographic imaging method according to an embodiment of this invention.

Endoscopic X-ray luminescence computed tomographic imaging method in the presented embodiment is described detailed with reference to FIG. 5, which may include the following steps:

Step S1, Collecting Multi-angle Images (S11) The object fixing stage 321 is adjusted to an appropriate place for the X-ray luminescence computed tomographic imaging, by using the system operation and control module 41 of computing unit 4:

In detail, the detecting object is firstly fastened onto the object fixing stage 321. The object fixing stage 321 is adjusted up and down in the vertical direction until it is located at the central height of C-shaped arm 311, through regulating the lifting platform 323 under the control of the stepping motor 324 which is controlled by the system operation and control module 41 of the computing unit 4. Next, the object fixing stage 321 slides along the horizontal direction under the adjustment of translational slide rail 322, which guarantee that the object fixing stage 321, the X-ray tube 11, and the X-ray CMOS flat detector 211 are collinear. Finally, the translational slide rail 322 and the lifting platform 323 are fine-tuned to ensure that the object fixing stage 321 is always in the radiation field of X-ray tube 11 and the imaging range of X-ray CMOS flat detector 211 when the C-shaped arm 311 slides evenly distributed in radian.

(S12) X-ray images and NIR light signal images in multi-angles are acquired via the system operation and control module 41 of the computing unit 4.

Firstly, the C-shaped arm 311 slides evenly spaced in a small angle (for example, the angle is no more than 3", and 3" is used in this embodiment) on the rotating control device 312, by controlling the stepping motor 314 with the system operation and control module 41 of the computing unit 4. It is obvious for those skilled persons in the art that the images can be acquired with variable interval angles.

Next, the X-ray tube 11 is turned on by the system operation and control module 41 of computing unit 4 for each angle, to irradiate the detecting object.

Finally, the NIR light signals emitted from the excited PNP probe inside the detecting object are gathered by using the NIR light signal collecting module 22 of the signal collecting unit 2; meanwhile, the X-ray images are also collected using the X-ray signal collecting module 21.

Step S2, Preprocessing Images (S21) The acquired NIR light signal image is preprocessed by using the image preprocessing module 42 of the computing unit 4, including but not limited to, the noise elimination, the extraction of the region of interest, and the dead pixel compensation.

(S22) The acquired X-ray image is preprocessed by using the image preprocessing module 42 of computing unit 4, including but not limited to, dead pixel compensation, noise elimination, and image correction.

Step S3, Executing Anatomical Structure Reconstruction

The preprocessed X-ray images are sparsely reconstructed by using the image reconstruction module 43 of the computing unit 4. The 3D volume data of the detecting object and the location of endoscopic detector 222 are then obtained. Afterwards, different organs are segmented from the volume data using organ segmentation algorithms, such as the man-machine interactive segmentation method integrated in 3DMED, so as to obtain the anatomical structure of the detecting object. It is obvious for those skilled persons in the art that the anatomical structure of the detecting object can be obtained by other methods.

Step S4, Executing 3D Optical Reconstruction

Incorporated with the preprocessed X-ray images, the accurate location and distribution information of target inside the detecting object is obtained from the preprocessed NIR light signal images, using the image reconstruction module 43.

Figure 6:
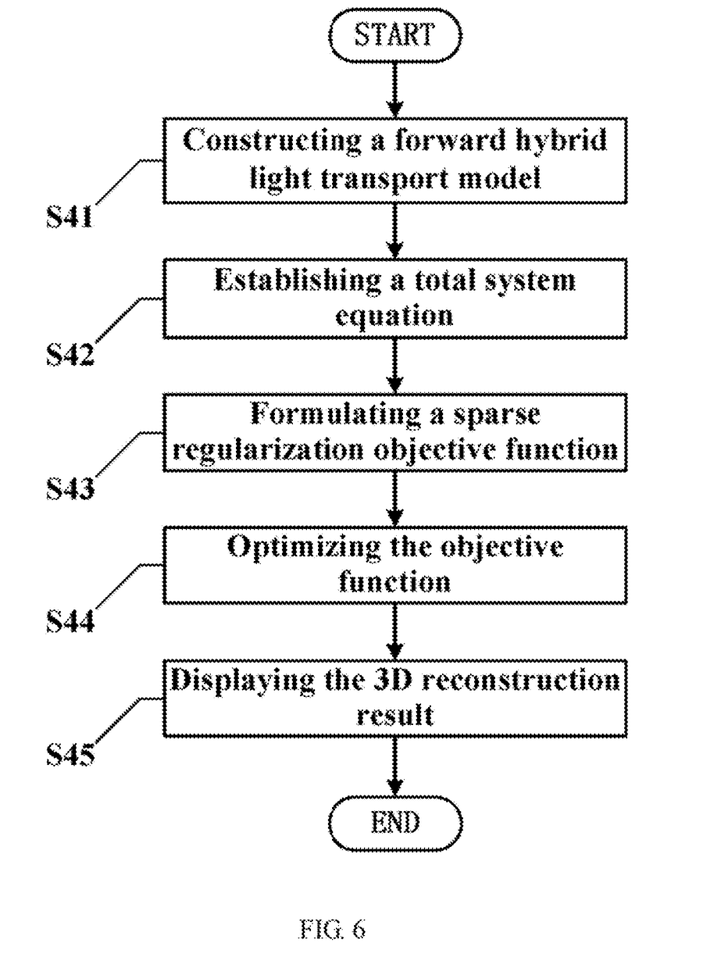
FIG. 6 shows a flow chart for 3D reconstruction of the internal target in the endoscopic X-ray luminescence computed tomographic imaging method according to an embodiment of this invention.

This step can be detailed as follows in reference to FIG. 6:

(S41) Constructing a forward hybrid light transport model

Based on the information of anatomical structure, optical properties, and location of the endoscopic detector 222, a hybrid $SP_3$-DE-FSE based forward light transport model for eXLCT could be constructed by using a refraction index boundary coupling condition.

Specifically, based on the anatomical structure of detecting object and the location of endoscopic detector 222 obtained in Step S3, biological tissues are classified into three categories, the low scattering, the high scattering and the cavity tissues according to tissues' optical properties. The classification rules can be generalized as follows.

Firstly, a coarse classification is conducted based on the specific location of tissues. Tissues where the PNP probe locates and the body surface belongs are classified into the low scattering tissue, while tissue where the endoscopic detector 222 locates when collecting the NIR light signals is defined as the cavity tissue.

Secondly, a fine classification is conducted based on the optical properties of tissues. Biological tissues can be classified into different scattering ones using Eq. (1) and the following rule:

$$\nabla = \frac{\mu'_s}{\mu_a} \quad (1)$$

where $\nabla$ is a classification criterion factor for different scattering tissues; $\mu'_s$ is a reduced scattering coefficient, and $\mu_a$ is a absorbing coefficient. If $\nabla \geq 10$, the biological tissue is classified into the high scattering tissue, and if $\nabla < 10$, the biological tissue is the low scattering tissue.

Thirdly, the NIR light transport in the three categories of tissues can be modeled separately by $SP_3$, DE, and FSE. The modeling process may execute according to the following rules. The $SP_3$ is utilized to describe the NIR light transport in the low scattering tissues, the DE is used for describe the NIR light transport in the high scattering tissues and the FSE is used for the NIR light transport from the boundary of cavity and scattering tissues to the endoscopic detector 222. The detailed description of the method of modeling is well-known in this field and can be ignored here.

Next, the boundary coupling condition is constructed to couple the $SP_3$, DE, and FSE. The forward light transport model for the eXLCT would be obtained by combining the process of PNP probe excited by the X-ray. For example, the process of PNP probe excited by the X-ray can be illustrated by Eq. (7), that is, a relationship among the concentration of PNP probe, the intensity of the X-ray and the emitted NIR light signal can be established according to Eq. (7) which would be incorporated in the light transport model.

The establishment for boundary coupling condition can be accomplished by the following steps.

Firstly, the coupling relation between the $SP_3$ and DE is established. Because both the $SP_3$ and DE are used to describe light transport in scattering tissues, that is, a diffuse light exists on the both sides of coupling boundary and the exit light flux rates of the $SP_3$ and DE are equal at coupling boundary. Herein, the exit light flux rate of $SP_3$ $J_{SP3}^+(r)$ at coupling boundary is:

$$J_{SP3}^+(r) = \beta_1(r)\phi_1(r) + \beta_2(r)\phi_2(r) \quad (2)$$

where r is an arbitrary point on the boundary of low and high scattering tissues; $\phi_1(r)$ and $\phi_2(r)$ are light flux components at r calculated by the $SP_3$, $\beta_1(r)$ and $\beta_2(r)$ are mismatched refractive indexes of the $SP_3$.

The exit light flux rate of DE $J_{DE}^+(r)$ at coupling boundary is:

$$J_{DE}^+(r) = \frac{\Phi(r)}{\alpha(r)} \quad (3)$$

where $\Phi(r)$ is a light flux at r calculated by the DE; $\alpha(r)$ is mismatched refractive index of the DE.

By solving Eq. (2) and Eq. (3) jointly and setting $J_{SP3}^{+}(r)=J_{DE}^{+}(r)$, a transformational relation of physical quantity at coupling boundary between the SP$_3$ and DE could be established, to realize coupling of light transport equations between the low and high scattering tissues:

$$\Phi(r)=\alpha(r)(\beta_1(r)\phi_1(r)+\beta_2(r)\phi_2(r)) \quad (4)$$

Moreover, the coupling relationship between the SP$_3$ or DE and the FSE can also be established.

In the eXLCT technique, the NIR light is emitted from the PNP probe, transported in the scattering tissues, then arrived at the boundary between the scattering and cavity tissues, and finally travels across the cavity tissue to the endoscopic detector. As a result, the diffuse light is changed into the non-diffuse light when arriving at the boundary of the scattering and the cavity tissues. Based on a free space light transport theory, the diffuse light will be transformed to a Lambertian source at the boundary and the light flux rate of Lambertian source is an exit light flux rate from the scattering tissues. Therefore, the coupling relationship between the scattering and cavity tissues is built by the following equation:

$$J(r) = \sigma\left(\frac{1}{\alpha(r)}\Phi(r)\right) + (1-\sigma)(\beta_1(r)\phi_1(r) + \beta_2(r)\phi_2(r)) \quad (5)$$

where r is the arbitrary point at the boundary of the scattering and the cavity tissues; $J(r)$ is the light flux rate at r and points inward of the cavity; $\sigma$ is the identify factor of scattering tissues, which is 0 if the low scattering tissue intersects with the cavity while 1 if the high scattering tissue intersects with the cavity.

Finally, the forward light transport model for eXLCT can be established based on the constructed boundary coupling condition and the excited process of PNP probe by the X-ray:

$B_1$, $B_2$, $C_1$, $C_2$, $D_1$ and $D_2$ are the parameters related to the boundary refractive index of the biological tissue; v is an outer normal vector at the outmost boundary of biological tissues; $\mu_\alpha{}'$ is the absorbing coefficient of the cavity; $P(r_d)$ is a light power acquired at endoscopic detector; $\theta_{r'}$ and $\theta_{r_d}$ are intersection angles between the surface normal vector at r', $r_d$ the direction vector from r' to $r_d$; $\xi(r',r_d)$ is visibility factor between r', $r_d$; $S(r)$ is a light flux density of the NIR light source formed by the NIR light emitted from the excited PNP probe, which depends on the intensity of X-ray irradiating onto the PNP probe $l(r)$, the concentration of PNP probe $\rho(r)$ and the yield efficiency from the PNP probe to the NIR light, and is calculated as:

$$S(r)=\in l(r)\rho(r) \quad (7)$$

(S42) Establishing a Total System Equation

Firstly, the forward light transport model constructed in Step (S41) is discretized using the finite element method (FEM). The system equation at the kth X-ray illuminating angle can be established by assembling the sub system equations at each discretized nodes:

$$A_k\rho=P_5 \quad (8)$$

where $A_k$ is a system matrix corresponding to the kth X-ray illuminating angle, depending on the distribution of three categories tissues in living body, the optical properties, and the location of the X-ray illuminating at body surface; $\rho$ is the concentration of PNP probe; $P_k$ is the calculated intensity of the NIR light at endoscopic detector corresponding to the kth X-ray illuminating angle.

The total system equation for eXLCT is then established by combining M system equations corresponding to M X-ray illuminating angles respectively:

$$A\rho=P \quad (9)$$

where A is the total system matrix and defined as $A=[A_1, A_2, \ldots, A_M]^T$, T is a matrix transposition operator; P is a calculated matrix of intensity of the NIR light signals at the endoscopic detector corresponding to M X-ray illuminating $$\begin{cases} \begin{cases} -\nabla \cdot \frac{1}{3\mu_{a1}(r)}\nabla\phi_1(r) + \mu_a(r)\phi_1(r) - \frac{2}{3}\mu_a(r)\phi_2(r) = S(r) \\ -\frac{2}{3}\mu_a(r)\phi_1(r) - \nabla \cdot \frac{1}{7\mu_{a3}(r)}\nabla\phi_2(r) + \left(\frac{4}{9}\mu_a(r) + \frac{5}{9}\mu_{a2}(r)\right)\phi_2(r) = -\frac{2}{3}S(r) \end{cases} & r \in \Omega_{LD} \\ \begin{cases} \frac{1+B_1}{3\mu_{a1}(r)}v\cdot\nabla\phi_1(r) - \frac{D_1}{\mu_{a3}(r)}v\cdot\nabla\phi_2(r) = -\left(\frac{1}{2}+A_1\right)\phi_1(r) + \left(\frac{1}{8}+C_1\right)\phi_2(r) \\ -\frac{D_2}{\mu_{a1}(r)}v\cdot\nabla\phi_1(r) + \frac{1+B_2}{7\mu_{a3}(r)}v\cdot\nabla\phi_2(r) = \left(\frac{1}{8}+C_2\right)\phi_1(r) - \left(\frac{7}{24}+A_2\right)\phi_2(r) \end{cases} & r \in \partial\Omega_{LD} \\ -\nabla\cdot(D(r)\nabla\Phi(r)) + \mu_a(r)\Phi(r) = S(r) & r \in \Omega_{HD} \\ \Phi(r) + \alpha(r)D(r)(v\cdot\nabla\Phi(r)) = 0 & r \in \partial\Omega_{HD} \\ P(r_d) = \int_B J(r')\xi(r',r_d)\frac{\cos\theta_{r'},\cos\theta_{r_d}}{|r_d-r'|}\exp(\mu_a'|r_d-r'|)dB & r' \in B_V, r_d \in R \\ \Phi(r) = \alpha(r)(\beta_1\phi_1(r) + \beta_2\phi_2(r)) & r \in B_{LH} \\ J(r') = \sigma\left(\frac{1}{\alpha(r')}\Phi(r')\right) + (1-\sigma)(\beta_1\phi_1(r') + \beta_2\phi_2(r')) & r' \in B_V \end{cases} \quad (6)$$

where $\Omega_{LD}$ and $\partial\Omega_{LD}$ are domains of the low scattering tissues and related boundary; and $\Omega_{HD}$ are $\partial\Omega_{HD}$ domains of the high scattering tissues and related boundary; $B_{LH}$ denotes a coupling boundary between the low and high scattering tissues; $B_V$ is a coupling boundary between the scattering and the cavity tissues; R is an acquisition point set of the endoscopic detector; $\mu_\alpha(r)$, $\mu_{\alpha 1}(r)$, $\mu_{\alpha 2}(r)$, $\mu_{\alpha 3}(r)$, and $D(r)$ are optical properties of the biological tissues; $A_1$, $A_2$, angles, defined as $P=[P_1, P_2, \ldots, P_M]^T$; M is the number of X-ray illuminating angles. Generally, the 3D reconstruction can be accomplished with the NIR light images collected at 1~5 X-ray illuminating angles.

(S43) Formulating a Sparse Reguarization Objective Function

A sparse regularization objective function can be obtained by combining the sparse distribution and nonnegative constrains of the PNP probe based on the difference between the calculated vector of the NPR light signals obtained in Step (S42) and the measurement vector detected by the endoscopic detector:

$$\rho = \arg \min_{\rho \geq 0} \ \|A\rho - P^m\|_1 + \lambda \|\rho\|_1 \qquad (10)$$

where $P^m$ is the measurement vector of NIR light signals detected by the endoscopic detector corresponding to M X-ray illuminating angles; $\lambda$ is a sparse regularization parameter; $\|F\|_1$ is $l_1$ norm of the matrix F.

(S44) Optimizing the Objective Function

The objective function formed in the Step (S43) can be solved by using appropriate optimization methods. The spatial location and distribution of the PNP probe inside the detecting object can be then obtained, indicating the location and distribution information of imaging target indirectly. It is obvious for those skilled persons in the art that the location and distribution information of target can also be those information of lesion or abnormal tissue inside the detecting object. Moreover, the distribution information usually provides the information such as the intensity of target.

(S45) Displaying the Three Dimensional Reconstruction Result

Image fusion of the reconstructed result of target obtained in Step (S44) and the anatomical structure of object from Step S3 is performed to obtain the three-dimensional image of the reconstructed target inside detecting object and display the three-dimensional image of the reconstructed target.

Although illustrative embodiments have been described herein in detail, those skilled in the art will appreciate that variations may be made without departing from the spirit and scope of this invention. Moreover, unless otherwise specifically stated, the terms and expressions used herein are terms of description and not terms of limitation, and not intended to exclude any equivalents of the systems and methods set forth in the following claims.

What is claimed is:

1. An endoscopic X-ray luminescence computed tomographic (eXLCT) imaging system, comprising:
   an excitation source unit (1) configured to excite a probe inside a detecting object from an external excitation source;
   a signal collecting unit (2) configured to collect X-ray images of the detecting object and near-infrared light signal images emitting from the probe being excited;
   a control unit (3) configured to collect the X-ray images of the object at different angles and to fix the detecting object and be adjusted to fit a field of X-ray imaging;
   a computing unit (4) configured to preprocess the collected X-ray images and the near-infrared light signal images, execute sparse reconstruction on the preprocessed X-ray images so as to obtain anatomical structure information of the detecting object and location information of an endoscopic probe in the signal collecting unit (2) inside the detecting object, and use the obtained anatomical structure information and the location information to execute three-dimensional optical reconstruction based on the preprocessed near-infrared light signal images so as to obtain localization and distribution of an imaging target inside the detecting object;
   wherein the signal collecting unit (2) comprises a near-infrared signal collection module, comprising a balloon imaging catheter (221), an endoscopic detector, a signal transmission fiber bundle (223) and a photomultiplier tube (PMT) array detector; and
   wherein the balloon imaging catheter comprises a medical catheter connected to an air delivery pipe in the signal transmission fiber bundle (223) at one end, and fastened to an outer surface of the signal transmission fiber bundle (223) at other end;
   wherein the endoscopic detector is wrapped by the medical catheter and the medical catheter is filled with air to hold up a cavity organ when collecting the near-infrared light signal images.

2. The system according to claim 1, wherein the endoscopic detector (222) comprises N pairs of drum lens (2221) and rod lens (2222); each pair of drum lens (2221) and rod lens (2222) is connected to a signal transmission fiber (2231) in the signal transmission fiber bundle (223), and configured to collect the emitted near-infrared light signal images from the probe.

3. The system according to claim 1, wherein the signal transmission fiber bundle (223) comprises N number of signal transmission fibers (2231) configured to transmit the collected near-infrared light signal images to the photomultiplier tube array detector (224); and an air delivery pipe (2232) configured to fill the balloon imaging catheter (221) with air.

4. The system according to claim 1, wherein the computing unit (4) includes an image reconstruction module (43) configured to
   construct a forward hybrid light transport model;
   establish a total system equation for the eXLCT imaging system based on the forward hybrid light transport model, to obtain calculation vectors of the near-infrared light signal images;
   formulate a sparse regularization objective function based on a difference between the calculation vectors of the NIR light signal images and a related measurement vector, and a combination of a sparse distribution and nonnegative constrains of the probe;
   optimize the objective function to obtain the spatial location and distribution of the probe inside the detecting object, indicating the location and distribution information of the imaging target.

5. The system according to claim 4, wherein the image reconstruction module (43) is further configured to construct the forward hybrid light transport model by: classifying biological tissues into low scattering tissues, high scattering tissues, and cavity tissues according to location information of the endoscopic detector inside the detecting object and optical properties of tissues;
   modeling near-infrared light propagation in the tissues with following propagation equations: a third-order simplified spherical harmonics equation ($SP_3$), a diffusion equation (DE) and a free space light transport equation (FSE) respectively; and
   constructing a boundary coupling condition to couple the propagation equations and constructing the forward hybrid light transport model for eXLCT along with the excitation of the probe by an X-ray beam.

6. The system according to claim 4, wherein the image reconstruction module (43) is further configured to establish -a total system equation by:

executing discretization on the constructed forward hybrid light transport model with a finite element method, to obtain sub system equations on each discretized element;

assembling the sub system equations as follows:

$$A_k \rho = P_k$$

where $A_k$ is a system matrix corresponding to a kth X-ray illuminating angle, depending on a distribution of the tissues in a living body, optical properties, and location of an X-ray illuminating at a body surface; ρ is a concentration of the probe; $P_k$ is a calculated intensity of the NIR light signals at the endoscopic detector corresponding to the kth X-ray illuminating angle;

establishing the total system equation for eXLCT by combining M sub system equations corresponding to M X-ray illuminating angles:

$$A\rho = P$$

where A is a total system matrix and defined as $A=[A_1, A_2, \ldots, A_M]^T$, T is a matrix transposition operator; P is a calculated intensity of the NIR light signals at the endoscopic detector corresponding to M X-ray illuminating angles, defined as $P=[P_1, P_2, \ldots, P_M]^T$; M is the number of X-ray illuminating angles.

7. The system according to claim 4, wherein the image reconstruction module (43) is further configured to calculate ρ as a sparse regularization objective function by using a following equation:

$$\rho = \arg \min_{\rho \geq 0} \ \|A\rho - P^m\|_1 + \lambda \|\rho\|_1$$

where $P^m$ is a measurement vector of NIR light signals detected by the endoscopic detector corresponding to M X-ray illuminating angles; λ is a sparse regularization parameter; $\|F\|_1$ is $l_1$ norm of a matrix F; and solve the sparse regularization objective function to obtain the spatial location and concentration distribution of the probe, indicating the location and distribution information of the imaging target inside the detecting object.

8. The system according to claim 5, wherein the biological tissues is classified according to rules of defining regions where the probe locates, a body surface belongs, and regions where a ratio of a reduced scattering coefficient to absorbing coefficient is less than 10 as the low scattering tissues; defining regions where the ratio of the reduced scattering coefficient to absorbing coefficient is larger than 10 as the high scattering tissues; and defining the tissue where the endoscopic detector locates when collecting the near-infrared light signals as the cavity tissues.

9. The system according to claim 8, wherein the image reconstruction module (43) is further configured to model the near-infrared light propagation by using the $SP_3$ to characterize the near-infrared light propagation in the low scattering tissues;

using the DE to characterize the near-infrared light propagation in the high scattering tissues; and using the FSE to characterize the near-infrared light propagation from boundaries between the low and high scattering tissues and the cavity tissues to the endoscopic detector.

10. The system according to claim 8, wherein the image reconstruction module (43) is further configured to model the near-infrared light propagation by coupling equations of $SP_3$ and DE, which characterizes the near-infrared light propagation in the low and high scattering tissues respectively, with a following equation:

$$\Phi(r) = \alpha(r)(\beta_1(r)\phi_1(r) + \alpha_2(r)\phi_2(r))$$

where r is an arbitrary point on boundaries of low and high scattering tissues; Φ(r) is a light flux at r calculated by the DE; $\phi_1(r)$ and $\phi_2(r)$ are light flux components at r calculated by the $SP_3$; α(r) is mismatched refractive index of the DE; $\beta_1(r)$ and $\beta_2(r)$ are mismatched refractive indexes of the $SP_3$.

11. The system according to claim 8, wherein the image reconstruction module (43) is further configured to model the near-infrared light propagation by coupling light transport equations of the low and high scattering tissues and the cavity tissues with a following equation:

$$J(r) = \sigma\left(\frac{1}{\alpha(r)}\Phi(r)\right) + (1-\sigma)(\beta_1(r)\phi_1(r) + \beta_2(r)\phi_2(r))$$

where r is an arbitrary point at the boundary of the scattering and cavity tissues; J(r) is a light flux rate at r and points inward of the cavity tissues; σ is an identify factor of scattering tissues, which is 0 if the low scattering tissue intersects with the cavity tissues, and is 1 if the high scattering tissue intersects with the cavity tissues.

12. An imaging method for an endoscopic X-ray luminescence computed tomographic (eXLCT) imaging system of claim 1, the method comprising steps of:
 (a) collecting near-infrared light signal images emitted from a probe and X-ray images of a detecting object;
 (b) preprocessing the collected near-infrared light signal images and the X-ray images;
 (c) executing a sparse reconstruction on the preprocessed X-ray images to obtain structural information of the detecting object and localization information of an endoscopic detector;
 (d) executing 3D optical reconstruction of the preprocessed near-infrared light signal images by using the obtained information of the detecting object and the localization information of the endoscopic detector, so as to obtain location and distribution information of an imaging target inside the detecting object;
 (e) displaying the 3D reconstruction result obtained by fusing the reconstructed image and the structural information of the detecting object so as to display the reconstructed image three-dimensionally;
 wherein the step(d) further comprises steps of:
  (d1) constructing a forward hybrid light transport model;
  (d2) establishing a total system equation for the eXLCT imaging system based on the forward hybrid light transport model, to obtain a calculation vector of the near-infrared light signal images;
  (d3) formulating a sparse regularization objective function based on a difference between the calculation vector of the NIR light signal images and a related measurement vector, and a combination of the sparse distribution and nonnegative constrains of the probe; and
  (d4) optimizing the objective function to obtain a spatial location and distribution of the probe inside the detecting object, indicating the location and distribution information of the imaging target.

13. The method according to claim 12, wherein the Step d1 further comprises steps of classifying biological tissues into a low scattering, a high scattering, and a cavity tissues according to location information of the endoscopic detector inside the detecting object and tissues' optical properties;
modeling the near-infrared light propagation in the tissues with following propagation equations: a third-order simplified spherical harmonics equation ($SP_3$), a diffusion equation (DE) and a free space light transport equation (FSE) respectively; and
constructing a boundary coupling condition to couple the propagation equations and constructing the forward hybrid light transport model for eXLCT along with the excitation of the probe by the X-ray beam.

14. The method according to claim 13, wherein the Step d2 further comprises steps of:
executing discretization on the constructed forward hybrid light transport model with a finite element method, to obtain sub system equations on each discretized element;
assembling the sub system equations as follows:

$$A_k \rho = P_k$$

where $A_k$ is a system matrix corresponding to the kth X-ray illuminating angle, depending on a distribution of the tissues in a living body, optical properties, and location of the X-ray illuminating at a body surface; $\rho$ is a concentration of the probe; $P_k$ is a calculated intensity of the NIR light signals at the endoscopic detector corresponding to the kth X-ray illuminating angle;
establishing the total system equation for eXLCT by combining M sub system equations corresponding to M X-ray illuminating angles:

$$A\rho = P$$

where A is the total system matrix and defined as $A = [A_1, A_2, \ldots, A_M]^T$, T is a matrix transposition operator; P is a calculated intensity of the NIR light signals at the endoscopic detector corresponding to M X-ray illuminating angles, defined as $P = [P_1, P_2, \ldots, P_M]^T$; M is the number of X-ray illuminating angles.

15. The method according to claim 12, wherein the Step d3 further comprises step of calculating $\rho$ as a sparse regularization objective function by using a following equation:

$$\rho = \arg \min_{\rho \geq 0} \|A\rho - P^m\|_1 + \lambda \|\rho\|_1$$

where $P^m$ is a measurement vector of NIR light signals detected by the endoscopic detector corresponding to MX-ray illuminating angles; $\lambda$ is a sparse regularization parameter; $\|F\|_1$ is $l_1$ norm of a matrix F; and
the step d4 further comprises step of solving the sparse regularization objective function to obtain the spatial location and concentration distribution of the probe, indicating the location and distribution information of the imaging target inside the detecting object.

16. The method according to claim 13, wherein the biological tissues is classified according to rules of defining regions where the probe locates, a body surface belongs, and regions where a ratio of a reduced scattering coefficient to absorbing coefficient is less than 10 as the low scattering tissues; defining regions where the ratio of the reduced scattering coefficient to absorbing coefficient is larger than 10 as the high scattering tissues; and defining the tissue where the endoscopic detector locates when collecting the near-infrared light signals as the cavity tissues.

17. The method according to claim 13, wherein the step of modeling the near-infrared light propagation further comprises steps of
using the $SP_3$ to characterize the near-infrared light propagation in the low scattering tissues;
using the DE to characterize the near-infrared light propagation in the high scattering tissues; and
using the FSE to characterize the near-infrared light propagation from boundaries between the low and high scattering tissues and the cavity tissues to the endoscopic detector.

18. The method according to claim 17, wherein the step of modeling the near-infrared light propagation further comprises step of coupling equations of $SP_3$ and DE, which characterizes the near-infrared light propagation in the low and high scattering tissues respectively, with a following equation:

$$\Phi(r) = \alpha(r)(\beta_1(r)\phi_1(r) + \beta_2(r)\phi_2(r))$$

where r is an arbitrary point on boundaries of low and high scattering tissues;
$\Phi(r)$ is a light flux at r calculated by the DE; $\phi_1(r)$ and $\phi_2(r)$ are light flux components at r calculated by the $SP_3$; $\alpha(r)$ is mismatched refractive index of the DE; $\beta_1(r)$ and $\beta_2(r)$ are mismatched refractive indexes of the $SP_3$.

19. The method according to claim 17, wherein the step of modeling the near-infrared light propagation further comprise step of coupling light transport equations of the low and high scattering tissues and the cavity tissues with a following equation:

$$J(r) = \sigma\left(\frac{1}{\alpha(r)}\Phi(r)\right) + (1 - \sigma)(\beta_1(r)\phi_1(r) + \beta_2(r)\phi_2(r))$$

where r is an arbitrary point at the boundaries of the low and high scattering and the cavity tissues; J(r) is a light flux rate at r and points inward of the cavity tissues; $\sigma$ is an identify factor of scattering tissues, which is 0 if the low scattering tissue intersects with the cavity tissues, and is 1 if the high scattering tissue intersects with the cavity tissues.

* * * * *

UNITED STATES PATENT AND TRADEMARK OFFICE
CERTIFICATE OF CORRECTION

PATENT NO. : 10,034,647 B2  Page 1 of 1
APPLICATION NO. : 14/379732
DATED : July 31, 2018
INVENTOR(S) : Jimin Liang et al.

It is certified that error appears in the above-identified patent and that said Letters Patent is hereby corrected as shown below:

In the Claims

Column 16, Claim 10, Lines 5-6:
"$\Phi(r) = \alpha(r)(\beta_1(r)\phi_1(r) + \alpha_2(r)\phi_2(r))$" should read
-- $\Phi(\mathbf{r}) = \alpha(\mathbf{r})(\beta_1(\mathbf{r})\phi_1(\mathbf{r}) + \beta_2(\mathbf{r})\phi_2(\mathbf{r}))$ --.

Column 16, Claim 12, Line 51:
"step(d)" should read -- step (d) --.

Column 17, Claim 15, Line 54:
"*M*X-ray illuminating" should read -- *M* X-ray illuminating --.

Column 17, Claim 15, Line 54:
"λ is a" should read --; λ is a --.

Signed and Sealed this
Twenty-seventh Day of August, 2019

Andrei Iancu
*Director of the United States Patent and Trademark Office*